United States Patent
Marx et al.

(10) Patent No.: US 9,795,361 B2
(45) Date of Patent: Oct. 24, 2017

(54) DEVICE FOR ASSISTING WITH THE HANDLING OF AN INSTRUMENT OR TOOL

(75) Inventors: Anja Marx, Paris (FR); Guillaume Morel, Bry S/ Marne (FR); Marie-Aude Vitrani, Bry-sur-Marne (FR); Serge Louis Wilfrid Muller, Guyancourt (FR); Răzvan Gabriel Iordache, Paris (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 811 days.

(21) Appl. No.: 13/410,727

(22) Filed: Mar. 2, 2012

(65) Prior Publication Data

US 2013/0231561 A1    Sep. 5, 2013

(30) Foreign Application Priority Data

Mar. 2, 2011    (FR) ...................... 11 51687

(51) Int. Cl.
*A61B 8/00* (2006.01)
*G05B 13/02* (2006.01)

(52) U.S. Cl.
CPC .......... *A61B 8/4209* (2013.01); *A61B 8/4218* (2013.01); *G05B 13/02* (2013.01); *G05B 2219/36432* (2013.01)

(58) Field of Classification Search
CPC .............. A61B 8/4209; A61B 19/5244; A61B 19/5248; A61B 5/06; B25J 9/1679; G05B 13/02; G05B 2219/36432
See application file for complete search history.

(56) References Cited

U.S. PATENT DOCUMENTS

| 5,078,140 A | 1/1992 | Kwoh |
| 6,204,620 B1 | 3/2001 | McGee et al. |
| 6,246,200 B1 | 6/2001 | Blumenkranz et al. |
| 6,374,157 B1 * | 4/2002 | Takamura ..................... 700/245 |
| 6,623,431 B1 | 9/2003 | Sakuma et al. |

(Continued)

FOREIGN PATENT DOCUMENTS

| CN | 1243690 A | 2/2000 |
| CN | 1522671 A | 8/2004 |

(Continued)

OTHER PUBLICATIONS

FR Search Report and Written Opinion dated Nov. 9, 2011 which was issued in connection with the French Application No. 1151687 which was filed on Mar. 2, 2011.

(Continued)

*Primary Examiner* — Amanda Lauritzen Moher

(57) ABSTRACT

A device for assisting with the handling of an instrument or tool, the device comprising a jointed mechanical structure on a support, wherein an instrument or tool may be attached, motor drives configured to actuate the jointed mechanical structure, according to a number of degrees of freedom of less than that which the structure provides to the instrument or tool, and an automatic control, wherein the automatic control drives the motor drives in order to facilitate the meeting of a constraint on position and/or velocity parameters of the instrument or tool, which constraint the motor drives by themselves, independently of handling by an operator, cannot entirely meet.

20 Claims, 3 Drawing Sheets

(56) References Cited

U.S. PATENT DOCUMENTS

| | | |
|---|---|---|
| 7,129,666 B2 | 10/2006 | Bauer et al. |
| 8,004,229 B2 | 8/2011 | Nowlin et al. |
| 8,160,205 B2 | 4/2012 | Saracen et al. |
| 2001/0001132 A1 | 5/2001 | Funda et al. |
| 2002/0082612 A1* | 6/2002 | Moll et al. .................. 606/130 |
| 2003/0013949 A1 | 1/2003 | Moll et al. |
| 2003/0220541 A1 | 11/2003 | Salisbury, Jr. et al. |
| 2005/0089205 A1 | 4/2005 | Kapur et al. |
| 2006/0020279 A1* | 1/2006 | Chauhan et al. ............ 606/167 |
| 2007/0021733 A1 | 1/2007 | Hasser et al. |
| 2007/0151389 A1 | 7/2007 | Prisco et al. |
| 2009/0088639 A1 | 4/2009 | Maschke |
| 2010/0041991 A1 | 2/2010 | Roundhill |
| 2010/0204828 A1* | 8/2010 | Yoshizawa ............ B25J 9/1666 700/245 |
| 2011/0144658 A1* | 6/2011 | Wenderow et al. ......... 606/130 |
| 2014/0039314 A1 | 2/2014 | Stoianovici et al. |

FOREIGN PATENT DOCUMENTS

| | | |
|---|---|---|
| JP | 02172452 A | 7/1990 |
| JP | 2005125080 A | 5/2005 |
| JP | 2010082333 A | 4/2010 |
| WO | 01/61618 A1 | 8/2001 |

OTHER PUBLICATIONS

Japanese Search Report issued in connection with corresponding JP Application No. 2012-042614 dated Dec. 25, 2015.

Unofficial English Translation of Chinese Office Action issued in connection with corresponding CN Application No. 201210063751.9 on Dec. 17, 2014.

Unofficial English Translation of Japanese Office Action issued in connection with corresponding JP Application No. 2012-042614 on Feb. 2, 2016.

\* cited by examiner

DEVICE FOR ASSISTING WITH THE HANDLING OF AN INSTRUMENT OR TOOL

BACKGROUND OF THE INVENTION

Field of the Invention

Embodiments of the invention relate generally to a device for assisting with the handling of an instrument or tool by means of a jointed mechanical structure. One particular embodiment of the invention relates to imaging, more particularly, imaging within the scope of a breast echographic examination of abnormalities detected in breast tomosynthesis.

Description of Related Art

Tomosynthesis is an x-ray imaging method with which it is possible to obtain a three-dimensional representation (3D) of an object of interest in the form of a series of successive cuts. These cuts are reconstructed from projections of the object of interest under various angulations.

To do this, the object of interest is generally placed between a source emitting X-rays and a detector of X-rays. The source and/or the detector are mobile, so that the direction of projection of the object on the detector may vary (typically over an angular range of 30°). Several projections of the object of interest are thereby obtained under different angulations, from which it is possible to reconstruct a three-dimensional representation of the object of interest, generally by a back-projection method well-known to the person skilled in the art.

Tomosynthesis is particularly used in screening and diagnosing breast cancer. In this case, this is referred as breast tomosynthesis or 3D mammography. FIG. 1 schematically illustrates an imaging device 1 for acquiring two-dimensional (2D) projection images of an organ B and for reconstructing a 3D image of this organ by tomosynthesis.

X-rays from a source 4 are emitted according to different angulations towards the organ B. After having crossed the organ B, they are detected by a detector 3 forming a set of projection images.

A three-dimensional representation of the organ B, typically in tomographic cuts (images) parallel to the detector 3 is reconstructed by a tomographic reconstruction method well-known to the person skilled in the art.

As in conventional 3D mammography, the breast of the patient is in particular compressed between the detector 3 and a compression paddle 2 during the tomosynthesis examination. The practitioner will analyze tomographic cuts in order to detect a possible lesion. It may happen that the practitioner wishes to conduct an additional examination for example by means of an echographic probe over an area which he/she will have identified. Customarily, the mammary echography examination is carried out with the patient lying on her back or slightly turned to the side. The breast is not compressed.

In order to localize the lesions to be evaluated with the echographic probe, the radiologist has to mentally "superpose" the 3D tomosynthesis image over the breast of the patient. This superposition is very difficult, since the patient is standing (or sitting) with the breast compressed in tomosynthesis and lying on her back with the breast which is not compressed in echography.

A solution to this problem is to carry out the echographic examination straightaway after the tomosynthesis examination, with the patient in the same position. The breast of the patient is compressed before the tomosynthesis examination and decompressed once the echographic examination is finished. The tomosynthesis system should be equipped with a compression paddle compatible with echographic examination (the paddle should be "transparent" to sound waves emitted by the echographic probe).

In that case, the images acquired by the echographic probe and the tomographic cuts correspond to a same position of the breast of the patient.

However, in order to bring the probe to the level of the possible lesion, the practitioner has to use tomographic images as a reference for localizing the lesion.

This is not without difficulty since the practitioner has to mentally reconstruct the localization in the space of the possible lesion from tomographic images.

Devices which provide assistance to a user during the handling of an instrument or tool are already known in robotics. To do this, the assistance device gives the possibility of imposing a kinematic constraint to the instrument or tool in order to position it so that the user may carry out a task. It is specified that by task is meant a defined action according to a certain number of degrees of freedom which the user wishes to exert with the instrument or tool.

These devices today are complex, bulky and expensive given that they require many motor drives. Moreover assistance devices are known for which the jointed mechanical structure is actuated according to a number of degrees of freedom of less than that which the structure provides to the instrument or tool.

For example, in surgery, jointed arms are already known which will preposition the end of the arm on which the tool is jointed. Once the arm is thereby pre-positioned, the user may cause his/her tool to perform a particular movement of translation or rotation while the arm remains constrained in this position.

Such jointed arms however do not provide guidance of the user in the movement which he/she gives to the instrument or tool. In the particular case mentioned above, these known devices would not provide guidance in the positioning of the echographic probe. Indeed, the number of motor drives is not only less than the number of degrees of freedom of the tool but also less than the number of degrees of freedom required for accomplishing the task.

Therefore, there exists a need for a device for assisting with the handling of a tool or of an instrument by means of a jointed mechanical structure which is simple, inexpensive with a reduced number of motor drives but which allows actual guidance of the movement of the tool or of the instrument.

BRIEF SUMMARY OF THE INVENTION

An objective of an embodiment of the invention is to assist a practitioner for targeting and analyzing a lesion in a region of interest by means of an instrument or tool which allows an area including a possible lesion to be scanned.

According to one embodiment, the invention provides a device for assisting with the handling of an instrument or tool. The device comprises a jointed mechanical structure on a support, wherein an instrument or tool may be attached, motor drives configured to actuate the jointed mechanical structure according to a number of degrees of freedom of less than that which the structure provides to the instrument or tool and an automatic control, wherein the automatic control drives the motor drives in order to facilitate the meeting of a constraint on position and/or velocity parameters of the instrument or tool, which constraint the motor drives by themselves, independently of handling by an operator, cannot meet.

According to another embodiment, the invention provides an assembly. The assembly comprises a mammographic imaging device comprising a source of X-rays, a detector and a compression paddle; and a device configured to assist with the handling of an instrument or tool. The device comprises a jointed mechanical structure on a support, wherein an instrument or tool may be attached, motor drives configured to actuate the jointed mechanical structure according to a number of degrees of freedom of less than that which the structure provides to the instrument or tool and an automatic control, wherein the automatic control drives the motor drives in order to facilitate the meeting of a constraint on position and/or velocity parameters of the instrument or tool, which constraint the motor drives by themselves, independently of handling by an operator, cannot meet.

BRIEF DESCRIPTION OF THE SEVERAL VIEWS OF THE DRAWINGS

Other features and advantages of embodiments of the invention will become further apparent from the description which follows, which is purely illustrative and should be read with reference to the accompanying drawings, in which.

DETAILED DESCRIPTION OF THE INVENTION

Figure 1:
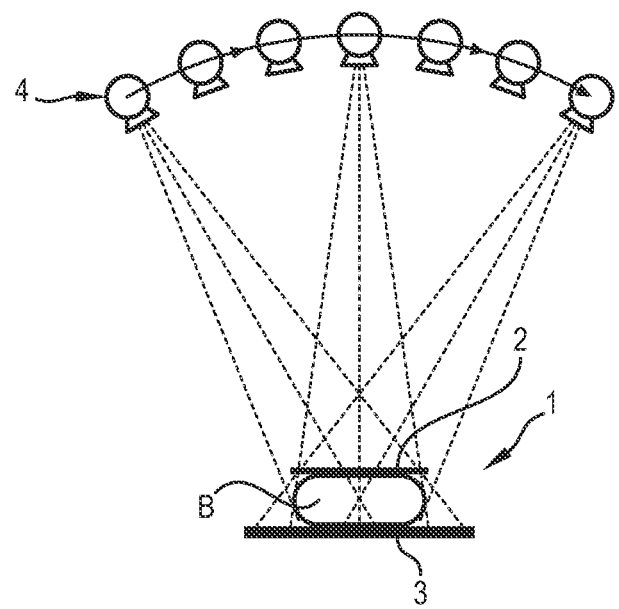
FIG. 1 schematically illustrates an imaging device for acquiring two dimensional (2D) projection images of an organ and for reconstructing a 3D image of this organ by tomosynthesis.
Figure 2:
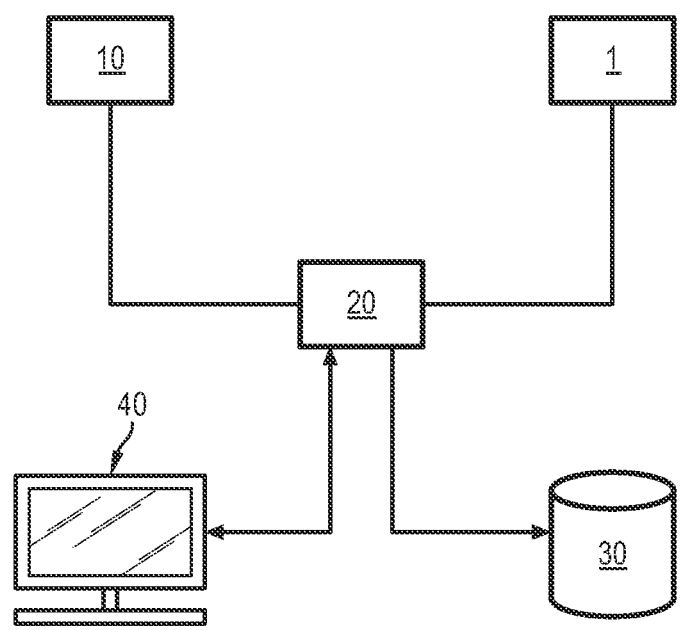
FIG. 2 illustrates a targeting and analysis assembly according to an embodiment of the invention.

FIG. 2 illustrates an assembly for targeting and analyzing a breast lesion of a patient. The targeting and analysis assembly comprises a medical imaging device 1 of the type of that of FIG. 1 as well as a device 10 for assisting with the handling of a tool or instrument such as an echographic probe S. The tool or the instrument may of course be any medical device which a practitioner may use for carrying out an examination or for proceeding with a surgical operation.

Figure 4:
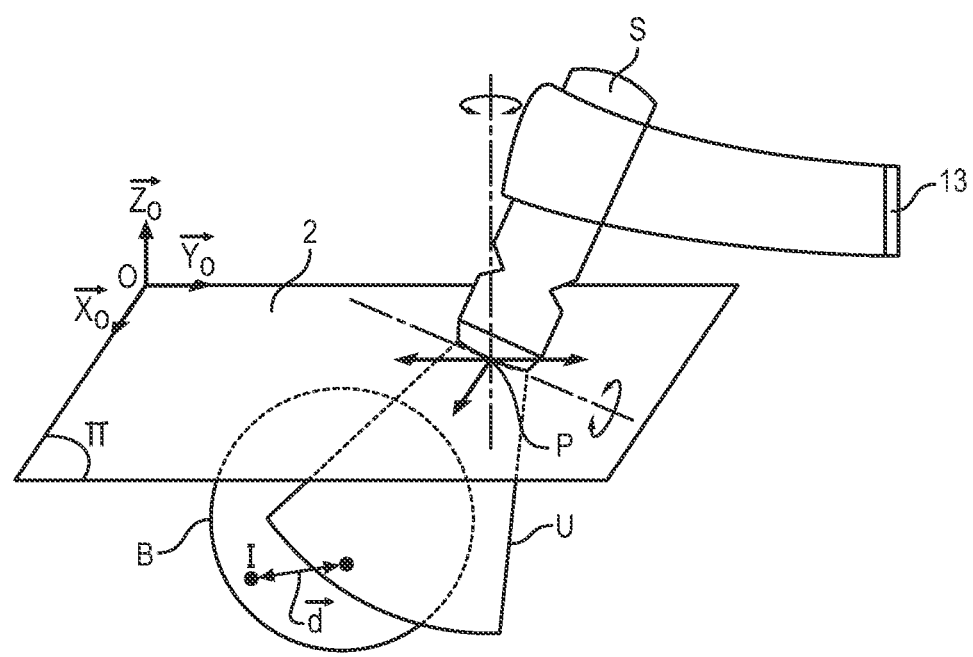
FIG. 4 illustrates the principle for assisting with the handling of an instrument or a tool according to an embodiment of the invention.

In the case of targeting and analyzing a lesion of the breast, the echographic probe allows acquisition of 2D images of the breast of the patient along an image plane U secant to a plane containing the compression paddle 2. FIG. 4 illustrates such a configuration. The targeting and analysis assembly comprises a unit 20 for acquiring and processing images acquired by the medical imaging device 1. Of course, both of these functions may be applied in two separate units.

This acquisition and processing unit 20 is programmed upon applying the processing method (for example for reconstructing a 3D image from 2D projection images). This may for example be a computer, a processor, a microcontroller, a micro-computer, a programmable automaton, one or more specific application integrated circuits, other programmable circuits, or other devices which include a computer such as a workstation.

Further, the acquisition and processing unit 20 is advantageously programmed for calculating the position of an object of interest such as a possible lesion of the breast of a patient and for calculating the stress which the assistance device 10 has to apply to the probe S. Alternatively, the calculation of the stress may be carried out beforehand with another device. Still alternatively, the position of an object of interest such as a possible lesion of the breast of a patient may be determined by the user on the basis of the image he/she views through the display unit 40.

The acquisition and processing unit 20 is coupled with a storage unit 8 which may be integrated or separate from the acquisition and processing unit 25. The storage unit 30 may be formed with a hard disc or any other removable storage means (a CD-ROM, a diskette, etc.). This may be a ROM/RAM memory of the processing and acquisition unit 20, a CD-ROM, a USB key, a memory of a central server.

The acquisition and processing unit 20 may comprise a reader device (not shown) for example a diskette reader or a CD-ROM reader, for reading the instructions of the processing method from a medium of instructions (not shown), such as a diskette or a CD-ROM. Alternatively, it may execute instructions of a processing method stored in firmware (not shown).

Finally, for displaying the images either from the medical imaging device 1 or from the echographic probe S, the targeting and analysis assembly comprises a display unit 40.

The display unit 40 is for example a computer screen, a monitor, a flat screen, a plasma screen or any type of commercially known display device. The display unit 40 allows a radiology practitioner to control the 3D representation of the breast (sampling of the volume, orientation of the cuts, etc.), and/or the display of the acquired 2D images as well as the targeting and analysis of a lesion by means of the echographic probe S.

Figure 3:
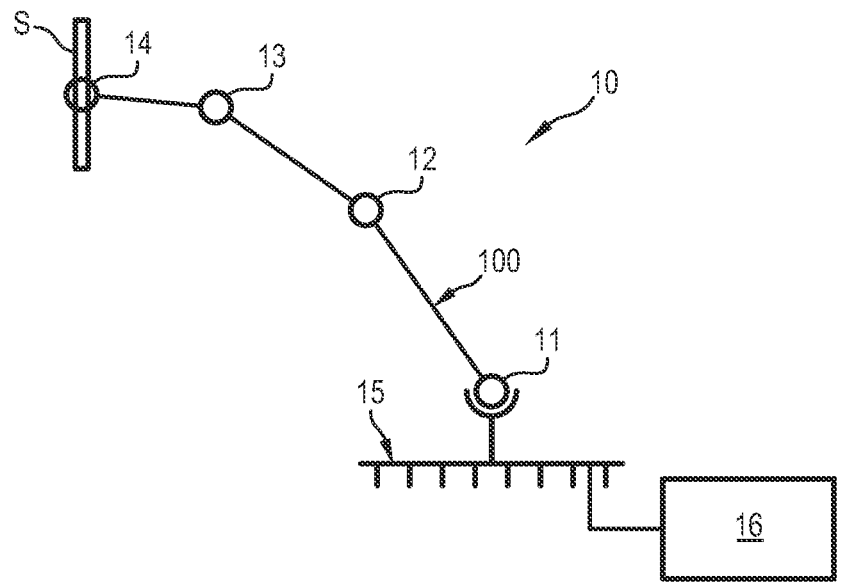
FIG. 3 illustrates a detailed view of an assistance device according to an embodiment of the invention.

FIG. 3 schematically illustrates a device 10 for assisting with the handling of an instrument or tool such as an echographic probe S. The assistance device includes a jointed mechanical structure 100 on a support 15. At its end 14 opposite to the support 15, the structure 100 bears the echographic probe S. Such a structure 100 is for example a jointed arm of the PHANTOM Omni robot type distributed by SensAble Technologies, Inc., Woburn, Mass. This structure 100 provides the echographic probe S with a certain number of degrees of freedom, in this case six.

It further has a certain number (three here) of motor drives 11, 12, 13 which actuate it according to a certain number of degrees of freedom, in this case three. Generally, the structure 100 has a number of motor drives which actuate the probe S according to a number of degrees of freedom of less than the number of degrees of freedom provided by the structure 100.

The assistance device further comprises an automatic motor drive control 16 which drives the motor drives according to a constraint on position and/or velocity parameters of the instrument. This driving facilitates the meeting of a constraint on the position and/or velocity parameters of the instrument. In particular, the position and/or velocity parameters of the instrument or tool S correspond to a greater number of degrees of freedom than that of the degrees of freedom on which the motor drives 11, 12, 13, act.

Indeed, the motor drives by themselves, independently of the handling by the user, cannot meet the constraint. With the assistance device, it is possible to assist the tool while meeting a constraint corresponding to a greater number of degrees of freedom than the number of degrees of freedom on which the motor drives 11, 12, 13, act.

In the case of assistance with the handling of the echographic probe S for targeting and analyzing a possible breast lesion of a patient, as this is illustrated in FIG. 4, the control 16 gives the motor drives 11, 12, 13 a set value tending to position the echographic probe S in the plane π of the compression paddle 2 of the medical imaging device 1 or in the vicinity of the plane π of the compression paddle 2, so that the possible lesion is visible by means of the echographic probe S.

Thus, it drives three motor drives 11, 12, 13 by setting a constraint thereto so that the echographic probe S is mobile according to four degrees of freedom (illustrated by the double arrows in FIG. 4) for the echographic probe S:

two translations on the compression paddle 2, a rotation along a vector normal to the compression paddle 2, a rotation around the intersection between the compression paddle 2, and an image plane U of the echographic probe S.

For example, the assistance provided by the jointed mechanical structure 100 is physically expressed by a force transmitted to the echographic probe S which depends on the position of the echographic probe S on the compression paddle 2. Although this single force is not sufficient for guiding the echographic probe in order to observe an arbitrary constraint, it was noticed that it is intuitively understood by the user as an indicator on how to handle the echographic probe S and that the thereby achieved partial guidance gave excellent results.

As already mentioned, the device for assisting with the handling gives the possibility of helping a practitioner to position an echographic probe S at the level of or in the vicinity of the possible lesion detected in the cuts from the medical imaging device 1. To do this, the echographic probe S is in contact with the compression paddle 2, P being a contact point. It is further held by the practitioner above its joint on the mechanical structure 100. It is according to the position of the possible lesion relatively to the probe S that the motor drives are driven by the control 16 of the assistance device.

The structure 100 includes movement sensors with which it is possible to know the position and orientation of the probe S in a reference system. Depending on this position and orientation, the processing unit 20 calculates the coordinates of the vector $\vec{d}$ connecting the possible lesion or target noted as I to its projection IU onto the image plane U. The control 16 receives as an input this vector $\vec{d}$ and drives the motor drives 11, 12, 13. Notably it drives these motor drives so that the structure 100 transmits at its joint 14 a force $\vec{F}$ to the probe S.

Figure 5:
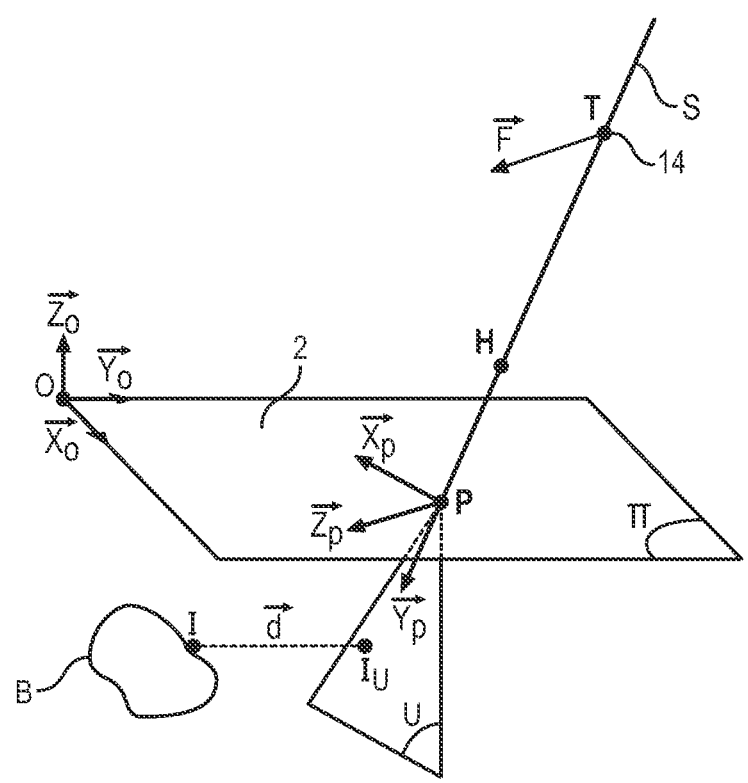
FIG. 5 illustrates the assistance with the handling of an instrument or a tool according to an embodiment of the invention.

According to the cases, such a force $\vec{F}$ depends on several parameters. For explaining the generation of the force $\vec{F}$, reference is made to FIG. 5. Two direct orthonormal reference systems are defined.

$F_p=(P, \vec{x}_P, \vec{y}_P, \vec{z}_P)$ a reference system of origin P, a point of the probe, this may for example be a contact point between the probe and the plane π containing the compression paddle 2, a reference system attached to the echographic probe S with $\vec{z}_P$ a vector normal to the image plane U of the echographic probe S and $\vec{y}_P$ the direction vector of the axis of symmetry of the ultrasound beam.

$F_O=(O, \vec{x}_O, \vec{y}_O, \vec{z}_O)$ a reference system of origin O attached to the plane π corresponding to the face of the compression paddle 2 on which the echographic probe S is handled with $\vec{z}_O$ a vector normal to the plane π.

The echographic probe S is maintained by the practitioner at the point H such that $\vec{PH}=-\|\vec{PH}\|\vec{y}_P$. The mechanical structure 100 applies a force $\vec{F}$ on the probe at point T such that $\vec{PT}=-\|\vec{PT}\|\vec{y}_P$. This point T corresponds to the junction between the probe and the jointed mechanical structure. This is the end 14 of the structure.

The force is zero when the image plane U of the probe S contains the possible lesion so as to let the practitioner handle the echographic probe S according to the degrees of freedom so that the possible lesion remains visible on the echographic image.

Further, the force is such that it increases when the echographic probe S moves away from the target I. The force $\vec{F}$ may in particular be selected in order to generate an elastic return if it is defined by $\vec{F}=k\vec{d}$ wherein k is a stiffness constant. The force includes three components defined in the reference system $F_O$ attached to the plane π.

Alternatively, in order to avoid perturbations at the contact between the echographic probe S and the compression paddle 2, the vertical component of the force along the axis $\vec{z}_O$ is zero. In this case the force $\vec{F}$ is expressed by $\vec{F}=k[\vec{d}-(\vec{d}\cdot\vec{z}_O)\vec{z}_O]$. For reasons of stability, it is desirable to damp oscillations at the end of the arm. In order to limit oscillations, the force $\vec{F}$ may be calculated by $$\vec{F} = k[\vec{d} - (\vec{d}\cdot\vec{z}_O)\vec{z}_O] + c\frac{\Delta\vec{d}}{\Delta t}$$

wherein c is a constant damping coefficient.

Still alternatively, the force may take into account the velocity $\vec{v}_T$ at the end 14 of the mechanical structure 100. In this case the force $\vec{F}$ is expressed by $$\vec{F} = k[\vec{d} - (\vec{d}\cdot\vec{z}_O)\vec{z}_O] + c\frac{\Delta\vec{d}}{\Delta t} + c_T\vec{v}_T$$

wherein $c_T$ is another damping constant.

Finally, the force $\vec{F}$ may relieve the practitioner from the weight of the echographic probe S. In this case the force $\vec{F}$ is expressed by $$\vec{F} = k[\vec{d} - (\vec{d}\cdot\vec{z}_O)\vec{z}_O] + c\frac{\Delta\vec{d}}{\Delta t} + \vec{c}_T\vec{v}_T + mg\vec{z}_0$$

wherein m is the mass of the echographic probe S and g is the standard gravity constant.

The device was experimentally tested with a first panel of users, which shows an improvement in terms of accuracy and duration of the gesture. Indeed, the average distance and the maximum distance between the image plane U of the echographic probe S and the target I are reduced by means of the device and the execution time is reduced.

What is claimed is:

1. A device for assisting with the handling of a tool or instrument, the device comprising:
   a jointed mechanical structure on which the tool or instrument is attached;
   a plurality of motor drives configured to actuate the jointed mechanical structure according to a number of degrees of freedom less than the total number of degrees of freedom of the jointed mechanical structure; and
   a controller configured to drive the plurality of motor drives, individually or in combination, in order to meet a constraint on at least one parameter of the tool or instrument that cannot be met independently of the tool or instrument being physically handled by an operator,
   wherein the at least one parameter of the tool or instrument corresponds to a number of degrees of freedom greater than the number of degrees of freedom on which the plurality of motor drives act, and
   wherein the controller is configured to transmit a force to the tool or instrument in order to indicate to the operator physically handling the tool or instrument how to move the tool or instrument in order to meet the constraint on the at least one parameter of the tool or instrument.

2. The device of claim 1, wherein the at least one parameter of the tool or instrument is position.

3. The device of claim 1, wherein the at least one parameter of the tool or instrument is velocity.

4. The device of claim 1, wherein the total number of degrees of freedom of the jointed mechanical structure is six and the plurality of motor drives are configured to actuate the jointed mechanical structure according to three degrees of freedom.

5. The device of claim 1, wherein the tool or instrument is an echographic probe.

6. The device of claim 1, wherein the force transmitted by the controller depends upon the at least one parameter.

7. The device of claim 1, wherein the jointed mechanical structure is an arm comprising a joint bearing and the force is transmitted to the tool or instrument at this joint.

8. The device of claim 1, wherein the force is transmitted by the controller to at least partially guide the operator physically handling the tool or instrument in reaching a lesion with the tool or instrument.

9. The device of claim 8, wherein the force transmitted by the controller increases as the tool moves away from the lesion.

10. An imaging assembly comprising:
    a mammographic imaging device comprising a source of x-rays, a detector, and a compression paddle; and
    a device for assisting with the handling of a tool or instrument, the device comprising:
      a jointed mechanical structure on which the tool or instrument is attached;
      a plurality of motor drives configured to actuate the jointed mechanical structure according to a number of degrees of freedom less than the total number of degrees of freedom of the jointed mechanical structure; and
      a controller configured to drive the plurality of motor drives, individually or in combination, in order to meet a constraint on at least one parameter of the tool or instrument that cannot be met independently of the tool or instrument being physically handled by an operator,
      wherein the at least one parameter of the tool or instrument corresponds to a number of degrees of freedom greater than the number of degrees of freedom on which the plurality of motor drives act, and
      wherein the controller is configured to transmit a force to the tool or instrument in order to indicate to the operator physically handling the tool or instrument how to move the tool or instrument in order to meet the constraint on the at least one parameter of the tool or instrument.

11. The assembly of claim 10, wherein the at least one parameter of the tool or instrument is position.

12. The assembly of claim 10, wherein the at least one parameter of the tool or instrument is velocity.

13. The assembly of claim 10, wherein the tool or instrument is an echographic probe.

14. The assembly of claim 10, wherein the force transmitted by the controller depends upon the at least one parameter.

15. The assembly of claim 10, wherein the jointed mechanical structure is an arm comprising a joint bearing and the force is transmitted to the tool or instrument at this joint.

16. The assembly of claim 10, wherein a vertical component of the force transmitted by the controller along an axis perpendicular to a plane containing the compression paddle is zero.

17. The assembly of claim 10, wherein the force is transmitted by the controller to at least partially guide the operator physically handling the tool or instrument in reaching a lesion with the tool or instrument.

18. The assembly of claim 17, wherein the force transmitted by the controller increases as the tool or instrument moves away from the lesion.

19. The assembly of claim 17, wherein the force transmitted by the controller is zero when an image plane of the tool or instrument contains the lesion and increases as the tool gradually moves away from the lesion.

20. The assembly of claim 17, wherein the force transmitted by the controller is elastic and is defined by:

$$\vec{F} = k\vec{d},$$

wherein k is a stiffness constant and wherein $\vec{d}$ is a distance between the tool or instrument and the lesion.

* * * * *